United States Patent [19]

Irlen

[11] Patent Number: 4,961,640

[45] Date of Patent: Oct. 9, 1990

[54] METHOD AND APPARATUS OF TREATMENT OF SYMPTOMS OF THE IRLEN SYNDROM

[76] Inventor: Helen L. Irlen, 4242 Country Club Dr., Long Beach, Calif. 90807

[21] Appl. No.: 756,935

[22] Filed: Jul. 19, 1985

Related U.S. Application Data

[63] Continuation of Ser. No. 410,045, Aug. 20, 1982, abandoned.

[51] Int. Cl.$^5$ ............................ G02C 7/10; A61B 3/00
[52] U.S. Cl. ........................................ 351/44; 351/246
[58] Field of Search ................................... 351/44–48, 351/163, 246

[56] References Cited

U.S. PATENT DOCUMENTS

| | | | |
|---|---|---|---|
| 2,057,983 | 10/1936 | Spitler et al. | 351/234 |
| 3,436,353 | 4/1969 | Dreyer et al. | 351/163 X |
| 3,445,153 | 5/1969 | Marks et al. | 351/163 |
| 4,247,177 | 1/1981 | Marks et al. | 351/44 |
| 4,381,136 | 4/1983 | Hosche et al. | 350/311 X |

FOREIGN PATENT DOCUMENTS 2307602 8/1974 Fed. Rep. of Germany ...... 351/163

OTHER PUBLICATIONS

Coblentz et al, Glasses for Protecting the Eyes from Injurious Radiations, Technologic Papers of the Bureau of Standards, May 1917.
Coblentz et al, Spectral-Transmissive Properties & Use of Colored Eye Protective Glasses, National Bureau of Standards, Jun. 1938.

Primary Examiner—Rodney B. Bovernick
Attorney, Agent, or Firm—Mason, Kolehmainen, Rathburn & Wyss

[57] ABSTRACT

Specially tinted lenses will provide substantial benefits to patients with various forms of visual disturbance caused by a recently identified functional disorder called the Irlen Syndrome of scotopic sensitivity, who show over-stimulation of receptor cells in the wavelength band of 425 to 575 nm. Symptomatically, the Irlen Syndrome is characterized by reduced visual resolution, impaired depth perception, impaired peripheral vision, and ocular vertigo. With use of the lenses the patients report improved visual resolution, increased comfort from reduced symptoms of eye strain, increased depth perception and peripheral vision, and reduced symptoms of ocular vertigo. The treatment includes experientially fitting the patient with lenses of an optimal color and transmission density, namely a predetermined attenuation in the 425–575 nm band. It has been determined according to the invention that pink and peach singly or in combination with blue, green, gray, purple, goldenrod, and yellow tints, can be effectively combined to achieve symptomatic relief. The color and density which is optimal for each patient must be determined individually for each patient and optimized as evaluated by pre-testing and post-testing on the Irlen Differential Perception Scale. Tinting and optical density are further optimized in each patient for near vision, far vision, and night vision.

18 Claims, 3 Drawing Sheets

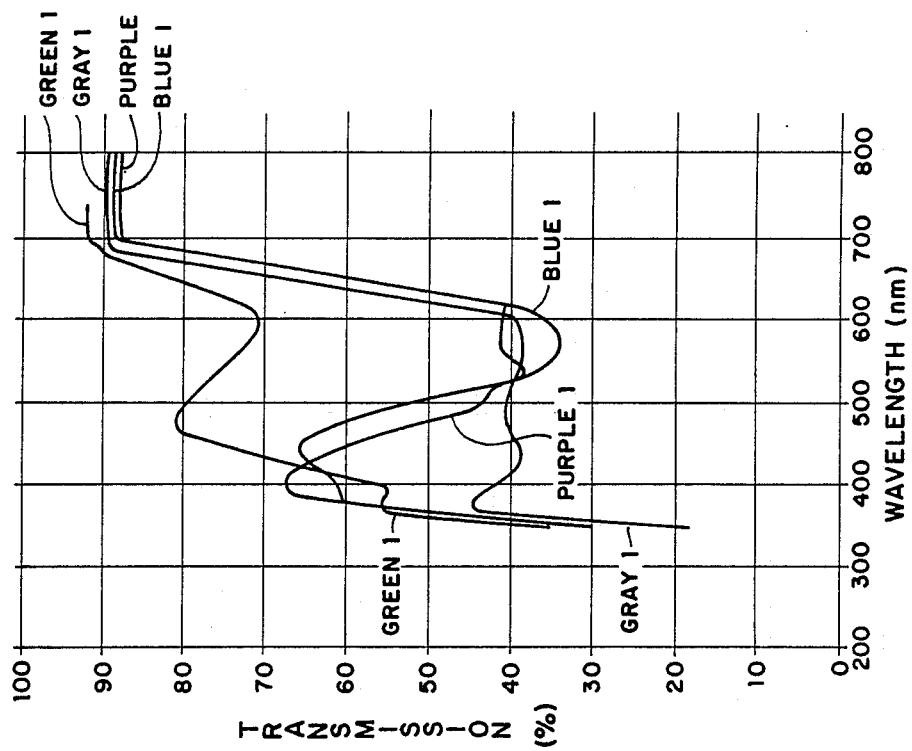
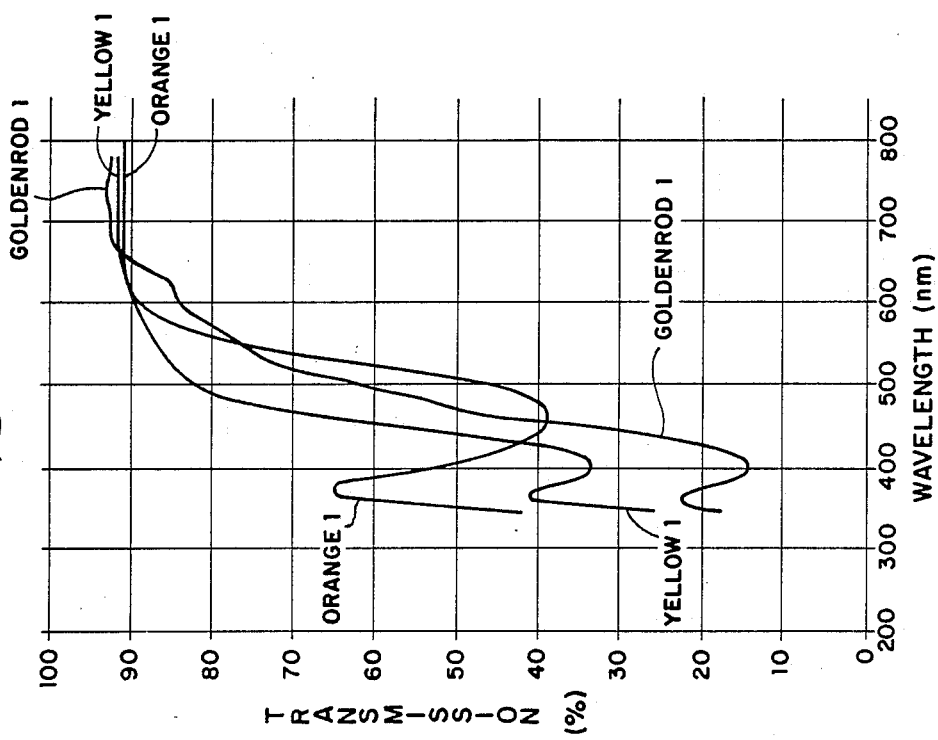

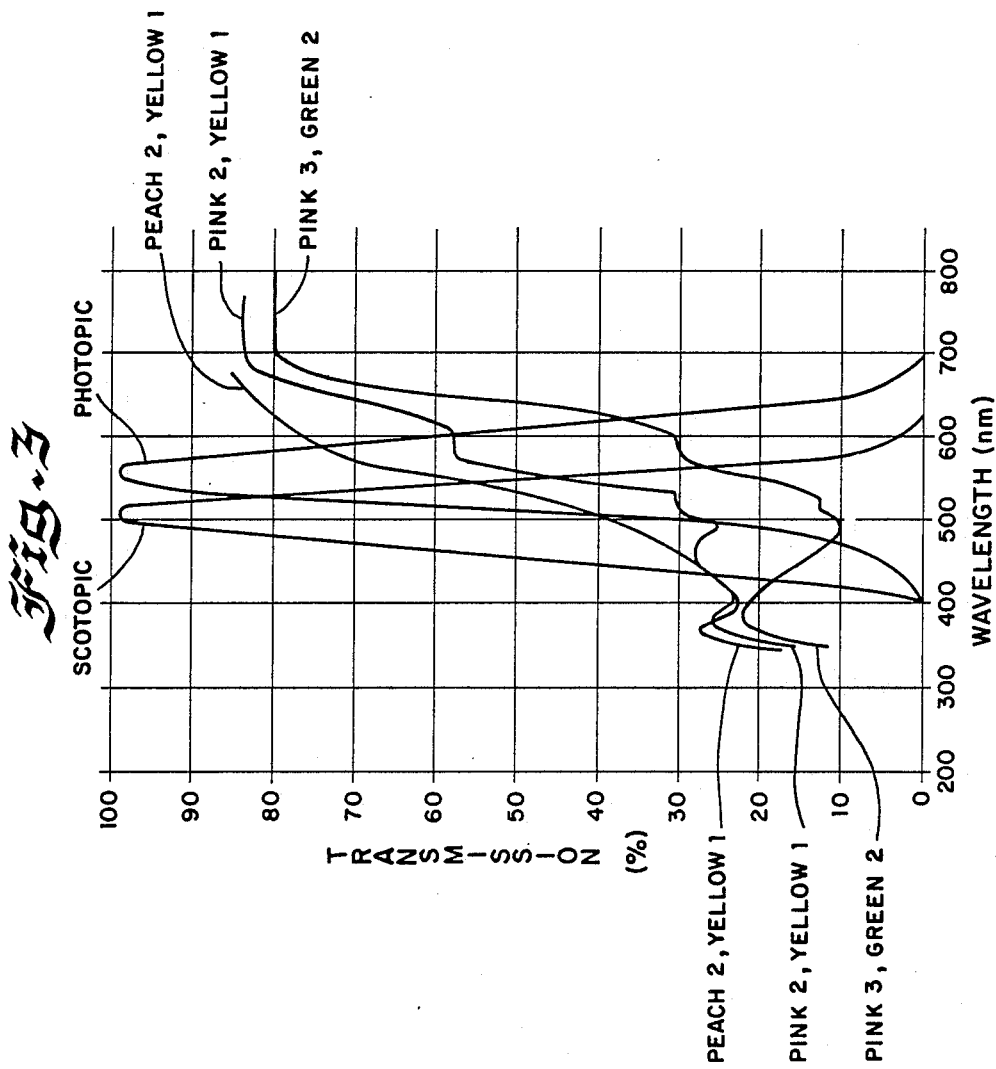

METHOD AND APPARATUS OF TREATMENT OF SYMPTOMS OF THE IRLEN SYNDROM

This application is a continuation of Ser. No. 410,045, filed Aug. 20, 1982, now abandoned.

BACKGROUND OF THE INVENTION

1. Field of the Invention

The present invention relates to the field of diagnosis and treatment of perceptual impairments, and in particular, relates to the treatment of reading-related or dyslexic impairments which are visual disturbances heretofore having an undiagnosed cause.

2. Description of the Prior Art

There are many perceptual impairments, particularly relating to learning disabilities, the causes of which are not understood. These impairments are symptomatically evidenced in a variety of ways which do not lead to a logically discernible categorization. These impairments or symptoms are referred to as dyslexia, which is loosely defined to include any impairment of the ability to read due to a brain defect.

Dyslexic impairments in children and adults substantially interfere with the patient's ability to adapt to conventional, formal education, and have far-reaching, lifelong social and economic implications for the patient.

The current treatment of dyslexia and related learning disabilities, as well as other forms of learning underachievement, are treated by a multi-disciplinary approach, from the arts of medicine, education, and psychology. Since dyslexia is currently believed to be a structural brain defect, as confirmed by a prior universal failure to derive any symptomatic relief for dyslexic patients through ocular treatment, the present state of treatment is directed to the central nervous system and brain. Ocular treatment is not expected, according to prior art experience, to have any effect on the brain's processing of visual stimuli. See, for example, American Academy of Ophthalmology Policy Statements, Ophthalmology Times, January 1982, at page 8–11.

The reason for this prior art belief is that children with dyslexia or related learning disabilities are observed to have the same incidence of ocular abnormalities, for example, refractive errors and muscle imbalance, including near-point convergence and binocular fusion deficiencies, as children without dyslexia. There is also no known peripheral eye defect that produces dyslexia and associated learning disabilities. Eye defects further do not cause reversal of letters, words or numbers. Recent studies suggest that dyslexia and associated learning disabilities may be related to genetic, biochemical, and/or structural brain changes. See, for example, University of Miami, "Chromosome 15 May Cause Dyslexia", Medical World News, Dec. 2, 1980, at p. 24; Shaywitz, et al., "The Biochemical Basis of Minimal Brain Dysfunction", Journal of Pediatrics 2:179–187, 1978.

According to the present state of the art, no known evidence supports any claim for improving the academic abilities of dyslexic or learning disabled children, or modifying delinquent or criminal behavior with treatment based on visual training, including: muscular exercises; ocular pursuit; tracking exercises; glasses (with or without prisms); neurologic organizational training, including laterality training and balance board; or perceptual training. Excluding correctable ocular defects, glasses (with or without prisms) have thus far been found to have no value in the specific treatment of dyslexia or any related learning disability.

Therefore, what is needed is a method of diagnosis and treatment which can assist in symptomatically treating and correcting the perceptual impairments that are suffered by dyslexic patients.

BRIEF SUMMARY OF THE INVENTION

The present invention is a method for the treatment of the above described perceptual impairments which are not correctable by the present state-of-the-art corrective lenses. The invention comprises the steps of identifying and characterizing symptomatic indicia of the perceptual impairments, particularly dyslexic impairments, and then interposing an optical filter or lens, having a selected transmission spectrum, between the eye of a patient having the perceptual impairments and an object perceived with the impairment. The filter attenuates by 60% or more all wavelengths substantially between 425 and 575 nm while still retaining sufficient transmittance in that range for all normal activities. Light outside the 425–575 nm range is not significantly attenuated.

The symptoms of the perceptual impairment are then compared by the patient when viewed through the optical filter with the symptoms when not viewed through the optical filter to determine if the symptoms have been ameliorated by use of the optical filter. Additional optical filters are repeatedly interposed between the eye of the patient and the viewed object, wherein each additional filter has a graduated difference in its transmission spectrum and/or optical density from each other optical filter. The interposition of such filters continues until the symptoms are minimized and the optimal transmission spectrum or tint and optimal optical density for the filter has been experimentally determined. Relief appears to be primarily dependent upon the tint provided by the filter, and only secondarily upon the optional density.

In particular, it has been determined according to the present invention that tinted glasses, having a primary tint of a pink or peach tint combined with blue, green, gray, purple, goldenrod and/or yellow tints of an experientially determined composite optical density often results in dramatic and effective relief of the perceptual impairments.

In addition to the method of treatment, the present invention also includes apparatus such as a pair of glasses having a frame and a pair of left and right lenses, or simply contact lenses, wherein the lenses are tinted by experientially determining an optimal transmission spectrum or tint and optical density for each lens for each eye of a patient, including possible adjustment for nearsightedness, farsightedness, and night vision. Glasses are also devised, according to the present invention, having lenses with distinguishably tinted upper and lower portions differentially characterized by the transmission spectrums and optical densities described above. In addition, the lenses can be differentially tinted between right and left eyes.

BRIEF DESCRIPTION OF THE DRAWINGS

FIG. 2a is a graph showing the transmittance spectrum of optical filters each characterized by one of a plurality of accessory tints classified in a first group.

FIG. 2b is a graph showing the transmittance spectrum of optical filters each characterized by one of a plurality of accessory tints classified in a second group.

FIG. 3 is a graph showing the transmission spectrums of three preferred combination of tints, as compared to the scotopic and phototopic sensitivity of the human eye.

DETAILED DESCRIPTION OF THE PREFERRED EMBODIMENTS

Figure 1B:
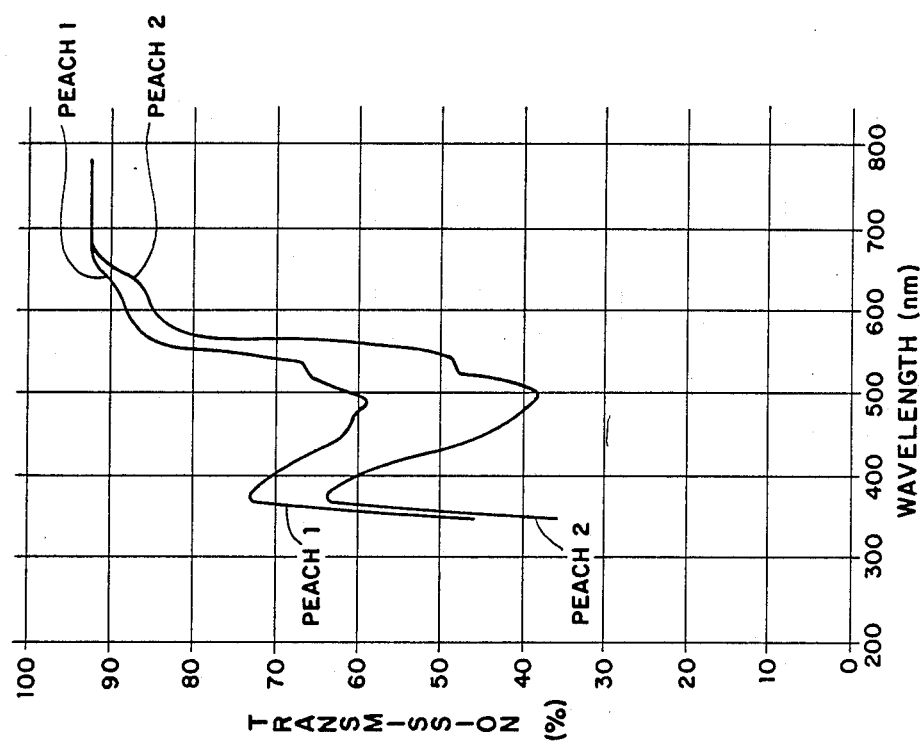
FIG. 1b is a graph of the spectral transmittance of a family of peach tinted filters: peach 1 and peach 2.

The present invention is a method for diagnosing and treating perceptual impairments including those resulting in dyslexia and other related learning disabilities. Where effective, the treatment is dramatically successful. The cause of dyslexia is not well understood, and the mechanism by which the method of the present invention serves to correct or alleviate the symptoms of some dyslexic patients is also not well understood, although it is related to overstimulation of the rods, particularly in the 425 to 575 nm wavelength band. The methodology of the present invention is not equally effective with all dyslexia patients. However, a large percentage (60-80%) of dyslexic patients who are diagnosed as having scotopic sensitivity report complete symptomatic relief. The methodology of the present invention further does not provide a permanent cure, but does provide symptomatic relief of the impairments as long as the lenses, which are prescribed by the present invention, are worn.

The present invention includes a method of experimentally correcting or relieving perceptual impairments and particularly the symptoms of dyslexia and other related learning impairments by experimentally fitting the patient with lenses wherein each eye is provided with an optical filter or lens of an appropriate tint and optical density. The exact tint and density required by each patient and each eye of each patient in order to provide symptomatic relief differs from one individual to another. A measured degree of attenuation is selectively provided in the 425 to 575 nm wavelength band.

The diagnosis of a patient as having perceptual impairments and the symptomatic relief achieved by the present invention is qualitatively measured and established as follows. A patient who has been diagnosed as dyslexic by conventional diagnosis is tested according to the Irlen Differential Perceptual Scale (IDPS). IDPS describes Irlen Syndrome, which manifests itself in four conditions: impaired depth perception, ocular vertigo, impaired peripheral vision, and reduced visual resolution. Ocular vertigo is symptomatically experienced as dizziness caused by refractive areas of the eye or imbalance of the intrinsic eye muscles. Peripheral vision is that vision more than 30° from the point of fixation in the central visual field.

The patient is fitted with a pair of empty frames of conventional design, into which a plurality of circular optical filters may be placed in front of each eye. The patient is then asked to focus on a printed page, musical page, math page, a close or far object, and any graphic design providing a means of testing visual resolution or perception.

Optical filters are then placed within the empty frame holders in front of each eye. One eye may be covered while the other is tested, and both eyes are tested simultaneously. If the patient wears conventional corrective lenses, the frame holder is of such a design that it fits over the corrective lens to allow testing while the patient wears his conventional corrective lenses.

The flat lenses or optical filters which are placed between the patient's eye and the test object are selected from a set, described below in connection with FIGS. 1-3, having a graduated series of colored tints and optical densities. Typically, each patient has an optimal selection of tint or tint combinations and optimal optical density, as determined by maximization of symptomatic relief. For example, if the patient views a printed page that has letters with shadows that overlap, colored filters are taken from the set of filters, until the perception of such overlapping shadows either disappears or is minimized. Usually, color combinations are experientially selected from the set of filters until maximum relief is achieved. The optical density of that color combination is then varied, or vice versa, to further enhance symptomatic relief, if possible. Relief appears to be primarily dependent upon the tint provided by the filter, and only secondarily upon the optical density. The patient is asked to report the symptoms of a particular impairment until the greatest minimization is found for all symptoms. The IDPS questionnaire is then retaken to qualitatively evaluate the effectiveness of the optimial lens combination.

During the diagnostic procedure, a plurality of differently tinted lenses as shown in FIGS. 1a, 1b, 2a, and 2n are superimposed between the eye of the patient and the perceived object. The combination of colors is varied until optimal relief from visual disturbance is achieved.

Although it is determined according to the present invention that a pink or peach tint appears to be necessary for a majority of the patients, usually the pink or peach tint is combined with optical filters of various densities having blue, green, gray, purple, goldenrod, and/or yellow tints.

Figure 1A:
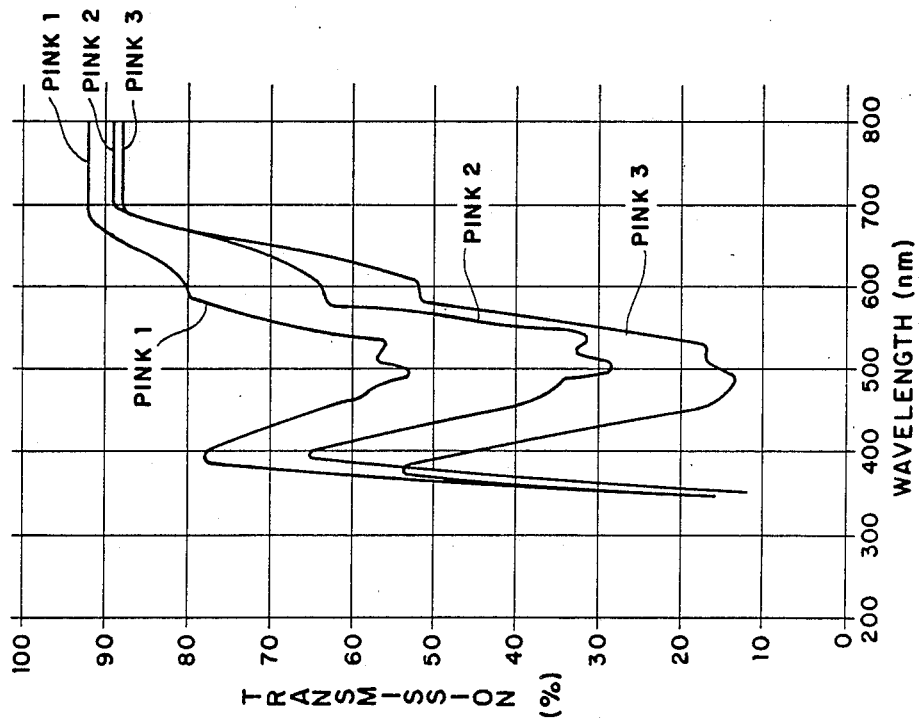
FIG. 1a is a graph of the spectral transmittance of a family of pink tinted filters: pink 1, pink 2, and pink 3, each having a different optical density.

Referring now to FIG. 1a, the spectral transmission of lenses designated as pink 1, pink 2 and pink 3 are graphically illustrated. The horizontal axis of the graph is the wavelength of light in nanometers, and the vertical axis indicates the percentage of transmittance. The spectral transmittance curves for the pink 1, pink 2, and pink 3 filters are roughly similar, with each characterized by a first maximum at approximately 400 nanometers, a minimum near 500 nanometers, increasing to a shoulder at approximately 675 nanometers. The differences between pink 1, pink 2, and pink 3 transmittance spectrums is in the height of the maximum and depth of the minimum. The transmittance in each case is higher at every point for pink 1 than for pink 2; and similarly, higher at every point for pink 2 than for pink 3. Each of the pink lenses is characterized by the property that there is a transmittance minimum between 425 nanometers and 575 nanometers. This is best illustrated in the case of pink 2, which has a first maximum transmittance at approximately 400 nanometers at 55% transmittance, and then declines sharply to a minimum transmittance of 22% at 500 nanometers. The transmittance again increases to 59% at 575 nanometers. This transmittance value is greater than twice the minimum transmittance in the range of 425 nanometers to 575 nanometers, which is 22% and occurs at 500 nanometers. The transmittance curve continues upwards to a first shoulder at approximately 600 nanometers at 62%, and thence to a second and final shoulder at 87%, just below 700 nanometers. Thus, for all wavelengths between 450 and 550 nanometers, 40% or more of the light is attenuated.

Similar sorts of shaped curves are also exhibited by pink 1 and pink 3, and by peach 1 and peach 2 in FIG. 1b.

Turning now to FIGS. 2a and 2b, symptomatic relief of visual impairments can often be maximized in patients exhibiting the Irlen Syndrome by combining one of the pink filters described in connection with FIGS. 1a or 1b with one or more accessory colored filters shown in FIGS. 2a or 2b. These accessory colors include goldenrod, green, blue, yellow, gray, purple, and orange. It must be understood, however, that many other colors could be employed in addition to those named, as long as such additional accessory colors have the same type of general spectral transmittance as shown in FIGS. 2a and 2b. In addition, each of the colors shown in FIGS. 2a and 2b are designated as number 1 filters for their respective color. In other words, FIG. 2 shows orange 1, goldenrod 1, and so forth. Deeper colors, such as goldenrod 2, yellow 2, purple 2, and so forth, and yellow 3, goldenrod 3 and green 3, could also be included and have the same relationship to each other to form a family of colors in a similar manner to that shown in FIGS. 1a and 1b with respect to pink 1, pink 2 and pink 3 and peach 1 and peach 2 respectively. Only the number 1 optical filters for the accessory colors has been shown in FIGS. 2a and 2b for the purposes of clarity.

In addition, the accessory colors divide into two groups. The colors of the first group shown in FIG. 2a are characterized by having a minimum transmittance in the range of 350–400 nm with substantially higher transmittances at all wavelengths above 450–550 nm. The colors of the second group shown in FIG. 2b are characterized by a minimum in the range of approximately 550–625 nm with substantially higher transmittances at all wavelengths above 625 nm. It has been determined that some patients are effectively treated only with one of the primary tints, peach or pink, in combination with an accessory color from only one of the above described groups and not from the other group of accessory colors. The basis for this distinction is unclear, although it is believed it may be related to individual defects in scotopic and photopic sensitivities.

Each of the accessory colors, while they exhibit a different spectral transmittance curve, are particularly characterized by a lower degree of transmittance between 425 nanometers and 575 nanometers than above 575. For example, goldenrod 1 has a first maximum of 14% transmittance at about 365 nanometers, a minimum transmittance of about 6% at 410 nanometers, and a rapidly increasing transmittance thereafter until a first shoulder of approximately 91% transmittance is reached near 700 nanometers.

In the range of wavelengths between 425 nanometers and 575 nanometers, the minimum transmittance occurs at 425 nanometers, which is about 25%. At 575 nanometers the transmittance is over 90%. Thus at 575 nanometers, the transmittance is greater than a factor of two the minimum transmittance in the range of 425 nanometers to 575 nanometers. The accessory optical filter orange one has its first maximum transmittance of approximately 56% at 370 nanometers, with a minimum transmittance of approximately 33% at about 470 nanometers, rapidly increasing to a shoulder of 91% transmittance, beginning at 600 nanometers. Each of the other accessories graphed in FIGS. 2a and 2b could likewise be graphed and described each having different valued maximum and minimums at different places within the visual spectrum between 350 and 800 nanometers.

Referring now to FIG. 3, a combination of pink and peach tints and one of the accessory tints is shown and graphed against the sensitivity of the rods and cones of the human eye. The scotopic sensitivity, or the sensitivity of the rods of the human eye, is a curve denoted by a single maximum at approximately 505 nanometers, dropping symmetrically on either side of the peak to less than 10% sensitivity at approximately 425 nanometers at the left side of the scotopic sensitivity curve, and approximately 580 nanometers at the right side. Similarly, the photopic sensitivity, or the sensitivity of the cones of the human eye, is shown as the right hand graph, with a maximum sensitivity at about 555 nanometers, falling off in a symmetric fashion on each side to 10% or less sensitivity to 475 nanometers on the left end of the curve and 650 nanometers at the right end of the curve. Thus, for rod receptor cells, the human eye is primarily sensitive to light between 425 and 575 nanometers with a maximum sensitivity at about 505 nm. Similarly, for the cone receptor cells, the human eye is primarily sensitive to light between 475 and 650 nanometers with a maximum sensitivity at about 555 nm. There is minimal sensitivity of any kind below 400 nanometers and above 700 nanometers.

Superimposed over the scotopic and photopic sensitivity of the human eye are composite transmittance curves for four combinations. The first combination is a combination of optical filters pink 3 superimposed with green 2. This combination exhibits a maximum at approximately 383 nanometers of about 22% and decreases to a minimum at about 495 nanometers of about 10% and rises thereafter. The spectral response of any of the optical filters can easily be determined from the data shown in FIGS. 1, 2a and 2b by taking the arithmetic product of each of the filters at each of the wave lengths. Similarly, the combination pink 2 and yellow 1 is the product of the transmittance of each of these separate filters. Again, the pink 2 and yellow 1 combination begins with a maximum at about 375 nanometers, decreasing to a minimum transmittance at 405 nanometers and increasing thereafter to shoulder. The combination for peach 2 and yellow 1 shows the transmittance through the lower portion of the 425–575 nanometer range to be substantially less steep than for the first three described combinations. In particular, peach 2/yellow 1 has a greater transmittance at all points above approximately 475 nm than the first three combinations. Thus, up to 55% of the rod stimulating light is transmitted at 550 nm by peach 2/yellow 1. Combination tints utilizing the accessory colors of goldenrod or yellow as illustrated in the case of yellow 1 in FIG. 3, appear to substantially attenuate light in the lower half of the scotopic sensitivity, i.e. 60% or more attentuation below 505 nm and allow 40% or more light through in the upper half of the scotopic sensitivity, i.e. above 505 nm. It should be noted that for each of the traces for the combination tints illustrated in FIG. 3, the transmittance at 575 nanometers is greater than twice the minimum transmittance in the range between 425 nanometers and 575 nanometers.

A comparison in the spectral response of these combinations of the pink and peach filters with one or more of the accessory colors illustrates that patients suffering from the Irlen Syndrome, which was only identified with the conception of the present invention, are provided with attenuated scotopic vision while providing substantially unattenuated photopic vision.

However, it has been found that it is not enough to simply block out scotopic vision in order to avoid the symptoms of the Irlen Syndrome. For example, Corning Glass Works, of Corning, N.Y., manufactures a photochromic filter lens with a 550 nanometer spectral cutoff under the trademark CPF 550. These lenses are effective in treating patients with retinal degenerative diseases and would therefore require visual protection from bright sunlight. These lenses are characterized by 5% transmittance or less for all wavelengths of 550 nanometers and lower. Transmittance arises sharply from 550 nanometers to at least 30% transmittance at 575 nanometers and 60% transmittance at 600 nanometers, with even higher percentage transmittance at wave lengths above 600 nanometers. Substantially all of the scotopic vision of a patient is cut off by the CPF 550 lenses. In addition thereto, a substantial portion of the photopic vision is also attenuated, namely only that portion of the color vision at 560 nanometers and above is transmitted to any appreciable extent. It has been determined that use of CPF 550 lenses do not provide any symptomatic relief to patients suffering from the Irlen Syndrome. Similarly, lenses devised according to the present invention do not provide the photophobic protection for patients suffering from retinal degenerative diseases.

A few case studies will further illustrate the utility of the present invention and its practice. The names have been changed to protect the privacy of the patients.

Case 1 - Anne

Anne is a woman age 21, who has had difficulties throughout her entire life with concentration and academic achievement. Conventional visual perceptual therapy has been sought and obtained by Anne without any significant benefit or progress. According to diagnosis rendered by the Scripps Institute at La Jolla, Calif., the patient demonstrated a selective impairment of her brain-sensitive adaptive abilities of the type suggesting an area of chronic, static and localized dysfunction in her left temporal region.

Anne suffers from perceptual impairments which include indefinite depth perception, such that substantially all three-dimensional aspects of the world about her are imperceptible. She suffers from hazy peripheral vision and is prone to many of the symptoms of eye strain, such as headaches, eyeaches, and eye muscle strain. Anne has a slow reading rate of approximately 90 words per minute, and, when she does read, the text is read word by word. In addition, Anne skips lines and words while reading. She complains of poor focus of printed units, that is, letters, numbers and musical notes, and states that the outlines of each of the units appear blurry. The maximum sustained attention and concentration interval while reading is approximately 15 to 20 minutes, after which the patient not only becomes frustrated, but begins to experience the symptoms of eye strain. As Anne looks at the printed page, the entire page is not in focus, and therefore only that section of the print within the focus range is clear, while the rest of page is blurred. The patient requires concentrated attention in order to keep the central area of focus readable, and to keep it from blurring. The difficulty of holding focus even on a word becomes greater as the cumulative reading time increases. She is unable to gain meaning from the printed page while reading. Anne also exhibits poor handeye coordination, and has difficulty with vertical and horizontal tracking of her eye movements.

Anne was then diagnosed with the IDPS test attached in Appendix 1, on which she scored 62% affirmative responses. Clear glass lenses, having no vision correction other than their tint and optical density, taken from the lens set specified in Table 1 above, were superimposed in a lens frame according to the method described above, until an optimal combination was achieved. In the case of Anne, it appeared that the symptoms described above were minimized by superimposition for both eyes of lenses pink 2 and green 1.

Anne was then given a conventional ophthalmological examination and it was determined that she had no evidence of eye pathology, nor need for any corrective lenses. The examination did reveal problems of depth perception, and vergency reserve. She was then fitted with tinted, non-corrected lenses having the optical density and color combination indicated above.

When fitted with the pink and green tinted lenses, the patient reported a dramatic improvement in depth perception with clear peripheral vision. The improvement in peripheral vision changed from essentially hazy peripheral vision to clear vision, as determined by self report. All symptoms of eye strain which occur during sustained reading periods were eliminated and the maximum concentration rate with the glasses exceeded two hours. Her reading rate increased from 90 words per minute without the glasses to immediately 110 words per minute with the glasses. As shown in the other cases reported below, reading rates usually increase by a substantially greater amount than for Anne. Anne is additionally hampered by central languge deficits, which significantly affect her reading rate. It is expected that the reading rate can further be improved by conventional educational treatment as the patient is taught to read word groups and phrases, now that the patient is able to focus on a group of print units of larger size. She is now able to comprehend what she is reading.

The patient reports that she no longer has difficulty in holding and sustaining focus on the print units. Focus increased from approximately 1% of the printed page without glasses to the entire page with the tinted glasses. The patient was able to perform vertical and horizontal tracking eye movements within normal parameters. There was also a concomitant improvement in hand-eye coordination, as evidenced by greater reported comfort and ability in driving an automobile, participation in sports and reading. For example, the patient previously reported apprehension when passing cars or changing lanes. She now feel comfortable in judging and estimating distances, and can park her car without hitting the curb. Whereas before she could not focus on the ball while playing tennis or racquetball, she now reports improvement in these sports, and can read without the use of a finger or a marker. Anne scored 5% affirmative on the Irlen IDPS questionnaire after fitted with the prescribed glasses.

Case 2 - Betty

Betty is a female aged 33, who suffers from impaired depth perception as measured by Titmis Fly test; complains of ocular vertigo; suffers from many symptoms of eye strain, such as headaches, eye muscle strain, reddening and watering of the eyes, and a sandy feeling in the eyes; reports hazy peripheral vision; demonstrates a reading rate of approximately 113 words per minute; exhibits a subnormal ability in horizontal and vertical eye tracking; reports difficulty of focus on printed units because of a shadowy or halo effect around the outline of each printed letter; reports symptoms of photophobia; exhibits sustained attention and concentration reading period of approximately 20 minutes; reads material a number of times in order to gain meaning; reports difficulty in obtaining and sustaining focus on a printed unit; reports the perception of dirt or bits of debris floating in her field of vision ("floaters"); and exhibits subnormal hand-eye coordination, as evidenced by uneasiness in ascending or descending stairs, driving an automobile, judging distance of oncoming traffic, and participation in sports where a moving ball is used, such as in tennis, bowling, hand ball, ping pong, and the like.

Betty was given a complete conventional ophthalmological examination, wherein it was determined there was no evidence of any eye pathology and that her corrective lenses were not necessary. Betty was wearing glasses with a prism for compensation for a weak eye muscle and some astigmatism. The ophthalmological examination also indicated inconsistent results in depth perception, fusion, vergency reserve, and muscle balance. Betty has been cross-eyed from birth, and began wearing corrective prescriptive lenses from the age of one year until the present. She participated regularly in ocular training eye exercizes under professional treatment from the age of 5 years to 18 years.

Betty was then tested in each eye using the superimposition of lenses from the set specified above for both near vision, far vision, and night vision. She scored 97% on the IDPS pre-test. It was experientially determined that the dyslexic symptoms described above were minimized in far vision with a combination of lenses of pink 3, gray 1, and green 1. Near vision symptoms were minimized with a combination of pink 3, gray 2, and green 1. Night vision or low level illumination vision were optimized by a combination of pink 2 and green 1. Betty was therefore fitted with two pairs of glasses. A first pair having a top half with the pink 3, gray 1, and green 1 composite tinting and density, and the bottom half characterized by a pink 3, gray 2 and green 1 tinting and density. The patient was also provided with a separate pair of glasses for night driving and vision in which the lens had the tints and density approximately equivalent to pink 2 and green 1. The tinting was done on clear glass and Betty does not need the prescription lenses with the prism. The prescriptive lenses with the prisms are per se ineffective in relieving Betty of any of the symptoms of Irlen Syndrome.

The patient reported a dramatic improvement in depth perception and appeared to exhibit three-dimensional perception within normal limitations as evidenced by self-report. Betty further reported elimination of all symptoms of eye strain during concentrated periods of reading, which were increased from the approximate 20 minute maximum period to more than three hours. The patient reported clear peripheral vision and no longer suffered from the symptoms of ocular vertigo. Reading rate instantaneously jumped from 113 words per minute without the glasses to 139 words per minute with the glasses. Again, conventional training can be expected over time to increase the reading rate further. She was able to read with meaning instead of having to reread material a number of times. With the glasses configured according to the present invention, Betty was able to track vertical and horizontal line movements within normal performance parameters, and reported adequate focus of printed words such that the outline of the letters was clear. The patient also reported and did not exhibit further symptoms of photophobia, difficulty in obtaining and sustaining focus on a printed unit, and further reported the disappearance of "floaters" from the field of vision. Concomitant improvement and hand eye coordination as evidenced by comfort in ascending and descending stairs, improved self-reported ability to identify details of shape, and greater ease in driving and parking. Betty scored 6% affirmative on the post IDPS questionnaire while wearing tinted glasses.

Case 3 - Cleo

Cleo is a female of age 35 who reports hazy peripheral vision and exhibits no depth perception according to the Titmus Fly test. Again, many symptoms of eye strain are reported, particularly during sustained periods of reading or focusing. Cleo has a reading rate of approximately 63 words per minute, and frequently skips lines and words while reading. When focusing on a printed unit, she reports that the outlines are blurry and have halos. The print units vibrate on the printed page and float about, and often exhibit multiple imaging, as many as four to eleven images to each unit. Cleo appears to be incapable of bringing the printed page into focus to any discernible extent, 1% page in focus, and has extreme difficulty with sustained attention and concentration while attempting to read. She reads textbooks five to six times in order to gain meaning from the printed page. She complains of the symptoms of ocular vertigo, exhibits poor vertical and horizontal eye movement tracking, and shows poor muscle balance between the eyes and an in ability to track both eyes together. As a result, Cleo was able to read only by covering one eye. Cleo reads different printed lines with each eye. She also exhibits poor hand-to-eye coordination, as evidenced by self-report inventory and exhibits the symptoms of photophobia.

Cleo wears conventional prescriptive lenses for presbyopia and astigmatism. A conventional ophthalmologic examination revealed problems of presbyopia, astigmatism, depth perception, muscle balance, fusion, and vergency reserve, but no evidence of eye pathology. Cleo has a muscular eye defect, called wandering eye, which was not discovered until age 11. Between the ages of 11 and 13 she participated in professional supervised eye training exercises, and used an eye patch. Cleo has had surgery for strabismus at the ages of 12, 13, 22 and 23, with only temporary improvement in vision.

Cleo was pre-tested with the IDPS diagnostic, and measured a score of 96%. She was then tested with superimposed lenses, as described above, in each eye for both near and far vision. Optimal color and density combinations were determined in each case. It has been determined that Cleo is effectively treated by a combination of peach 1 and yellow 2.

After being fitted with the glasses, the patient reported and exhibited a dramatic improvement in depth perception as measured by ability to walk off curbs, to see curbs and stair, and to judge distance while driving and parking. Cleo exhibited clear peripheral vision, 1% to 100% measured by self-report. The patient reported the elimination of many of the symptoms of eye strain when participating in concentrated and sustained periods of reading. The maximum periods of reading concentration increased from five minutes without the benefit of the glasses to more than one hour. The reading rate with just corrective lenses was measured at approximately 63 words per minute, and instantaneously thereafter with the addition of tinting at 117 words per minute. The patient, when reading, no longer skipped lines or words, and reported that the outlines of the letter were clear, that the triple images had disappeared, and that only one image for each print unit was perceived. The patient indicated that the letters no longer overlapped, and no longer formed multiple images, vibrated or floated on the printed page. She now can obtain meaning the first time instead of having to re-read material five to six times. Cleo further reported comfort and ease in obtaining and holding sustained focus on a print unit, together with the ability to read with both eyes. The patient further reported the ability to coordinate both eyes together to obtain the single image and reported a reduction in her sensitivity to light. In addition, Cleo indicated complete relief from feelings of ocular vertigo, and exhibited normal capacity to vertically and horizontally track eye movements with both eyes cooperatively moving together. She further evidenced an increasing ability of eye-to-hand coordination. Cleo scored 4% affirmatively on the IDPS questionnaire with the prescribed glasses.

The cases cited above included recent instances of treatment, and in the instance of Cleo in Case 3, one of the more acutely impaired patients. In one case, the patient was found to be visually disabled by the California Department of Rehabilitation and was provided wit a reader while in college at public expense. With lenses devised according to the present invention, this same patient is able to pursue a course of study without the assistance of a reader. Although each of the patients reported similar types of perceptual impairments causing dyslexia, the diagnosis and treatment with the invention is equally effective in treating perceptual impairments and other learning related problems other than those specifically set forth in the examples.

In each case, the tints and optical density found optimal for symptomatic relief were different for each patient, and in some cases, were found to differ for near-field, reading vision, for general vision, and possibly for night vision within a single individual. In each case, the reading rate is dramatically increased together with increased comprehension and the ability to expend concentrated effort for dramatically increased durations. Most significant is the ability to gain comprehension from the printed page while reading instead of having to re-read material a number of times. Headaches disappeared, and other symptoms of eye strain were greatly reduced or eliminated as well. Handwriting for each of the patients also immediately improved as well as mathematical computations practiced on a printed page.

The ability of patients to sight read music distinctly improved, together with reported relief from the symptoms of ocular vertigo. Patients thus treated reported objects changed from being seen as a flat plane to a three-dimensional sphere. It appears that binocular vision on the patients was substantially improved, with both eyes focusing together. In addition, with reported increase in eye comfort, the patients also reported improved visual resolution and exhibited increased comprehension of material that could now be read at a faster rate. "Floaters" in the field of vision disappeared, and the ability to hold numbers in horizontal and vertical columns increased, thus improving mathematical computational abilities. Similarly, the visual fixation of musical notes and musical staffs increased, together with improved performance in activities requiring hand-eye coordination.

The method of the present invention also appears to be effective in treating the symptoms listed below in addition to those reported in the cases above. For example, movement regression or the backward movement along the printed page; unequal time duration on word fixation, erratic and jerky eye movement; nystagmus, or rapid eye fluttering; alternate sighting between eyes; sluggish focusing mechanism; difficulty with eye fixation and coordinated movement; movement or pulsation of letters; difference in black shading of the print units; and inability to discern shading or shadowing gradiations; are additional dyslexic symptoms amenable to treatment according to the present invention. It should be understood that the listing is not exclusive and it is contemplated that many other dyslexic or learning related impairments could also be treated as described. In addition to dyslexic problems, symptoms relating to dyscalculia, depth perception, and ocular vertigo are treated equally as well. It should be noted that this treatment is remedial and no permanent correction is achieved. The lenses prescribed according to the present methodology must be worn at all times to achieve the beneficial effects.

When the treatment is effective, the improvement is so dramatic that in some cases the patient has psychological difficulty with the improvement. This is particularly the case with adults where the patient has lived an entire lifetime with an acute awareness of his impairments and has suffered from its disability. In some cases, these patients have come to perceive themselves as retarded or mentally impaired in some manner, only now to find this simple, effective physical remedy. Although dyslexic patients are characterized by severe learning disabilities, and therefore are often poor academic achievers, there is no reliable basis from which to conclude that intelligence and dyslexic disability are correlated to any extent, particularly when the dyslexic symptoms are removed or substantially alleviated by the present invention.

It must be clearly kept in mind that the diagnosis and methodology of the present invention described here are simply illustrative and should be taken by way of an example, and do not in any manner limit the scope and spirit of the invention as claimed. Many alterations and modifications may be made by one with ordinary skill in the art, once provided with the teachings of the present invention, which modifications and alterations do not depart from the spirit and scope of the claimed invention.

I claim:

1. A method for the treatment of perceptual impairments caused by scotopic sensitivity, comprising the steps of:

identifying and characterizing symptomatic indicia of said perceptual impairments;

sequentially interposing one or more optical filters between the eye of a patient having said perceptual impairments and an object perceived with said impairments, each said optical filter having a percentage attenuation of at least 60% at selected wavelengths within the range above 425 and below 575 nanometers and having a substantially higher transmittance at wavelengths above 575 nanometers and below 425 nanometers, with the transmittance at 575 nanometers being greater by at least a factor of 2 than the minimum transmittance in the range between 425 and 575 nanometers, said filters being graduated with respect to each other in their spectral characteristics;

comparing the symptomatic indicia of said perceptual impairments when viewing through each optical filter with said symptomatic indicia when not viewing through the optical filter to determine if said symptomatic indicia have been ameliorated; and identifying the filter or combination of filters that minimizes said symptomatic indicia to generate a prescription for the optimum filter for the patient.

2. The method of claim 1 wherein said step of interposing said optical filters between said eye of said patient and said object perceived with said perceptual impairments includes interposing graduated optical filters.

3. The method of claim 1 where said steps of interposing said optical filters includes interposing optical filters having graduated optical densities and substantially the same transmission spectrum.

4. The method of claim 1, where said step of interposing said optical filters includes interposing optical filters having graduated spectral characteristics with substantially constant optical densities.

5. The method of claim 1 where said steps of interposing and continually interposing said optical filters includes interposing optical filters having a tint selected from the group of pink and peach.

6. The method of claim 1 where said steps of interposing and continually interposing said optical filters includes interposing optical filters having a gray tint.

7. The method of claim 1 where said steps of interposing and continually interposing said optical filters includes interposing optical filters having a yellow tint.

8. The method of claim 1 where said steps of interposing and continually interposing said optical filters includes interposing optical filters having a purple tint.

9. The method of claim 1 where said steps of interposing and continually interposing said optical filters includes interposing optical filters having a goldenrod tint.

10. The method of claim 1 where said steps of interposing and continually interposing said optical filters includes interposing optical filters having a green tint.

11. The method of claim 1 where said step of interposing said optical filters includes interposing filters selected from the group of pink, blue, gray, peach, purple goldenrod and yellow tints.

12. The method of claim 1 where said step of interposing said optical filters includes interposing optical filters having a tint selected from the group of pink and peach, and in addition thereto, a superimposing optical filter selected from a group having blue, green, gray, purple goldenrod and yellow tints.

13. The method of claim 1 where said step of interposing said optical filters includes superimposing a plurality of optical filters having different transmission spectrums.

14. The method of claim 13 where said step of superimposing optical filters of differing color spectrums includes superimposing a plurality of optical filters selected from a group having pink, gray, peach, purple, goldenrod and yellow tints.

15. A method for reducing visual impairment caused by the sensitivity of a patient to one or more bands of wavelengths within the range of 425 to 575 nanometers comprising:

providing a plurality of filters each having an attenuation of at least 60% at a selected band of wavelengths within the range of 425–575 nanometers and a substantially higher transmittance above and below said selected band, with the transmittance at 575 nanometers being greater by at least a factor of 2 than the transmittance at the selected band of wavelengths, the selected band of wavelengths being different for various ones of said plurality of filters;

sequentially interposing selected ones of said filters between an eye of the patient and an object being viewed by the patient;

determining which filter or combination of filters most reduces the visual impairment of the patient when the object is viewed therethrough; and identifying the spectral characteristics of the filter or combination of filters that most reduces the visual impairment.

16. The method recited in claim 15 wherein the step of providing the plurality of filters includes providing a plurality of filters of different density for various ones of said selected bands.

17. The method recited in claim 1 further including the step of fabricating a single filter having the spectral characteristics defined by the prescription.

18. The method recited in claim 15 further including the step of fabricating a single filter having the spectral characteristics of the filter or combination of filters that most reduces the visual impairment.

* * * * *